(12) United States Patent
Kennedy et al.

(10) Patent No.: US 10,774,185 B2
(45) Date of Patent: Sep. 15, 2020

(54) CENTRALLY FUNCTIONALIZABLE LIVING CATIONIC POLYMER OR COPOLYMER AND METHODS OF SYNTHESIZING THE SAME

(71) Applicants: Joseph P. Kennedy, Akron, OH (US); Turgut Nugay, Sariver-Istanbul (TR); Nihan Nugay, Sariver-Istanbul (TR); Tejal J. Deodhar, Akron, OH (US); Susan Dollinger, Uniontown, OH (US)

(72) Inventors: Joseph P. Kennedy, Akron, OH (US); Turgut Nugay, Sariver-Istanbul (TR); Nihan Nugay, Sariver-Istanbul (TR); Tejal J. Deodhar, Akron, OH (US); Susan Dollinger, Uniontown, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 16/257,582

(22) Filed: Jan. 25, 2019

(65) Prior Publication Data
US 2019/0225757 A1 Jul. 25, 2019

Related U.S. Application Data

(60) Provisional application No. 62/621,848, filed on Jan. 25, 2018.

(51) Int. Cl.
*C08F 8/08* (2006.01)
*C08G 81/02* (2006.01)
(Continued)

(52) U.S. Cl.
CPC ............ *C08G 81/025* (2013.01); *C07C 13/45* (2013.01); *C07C 13/547* (2013.01); *C08F 4/16* (2013.01);
(Continued)

(58) Field of Classification Search
CPC .......... C07C 13/44; C07C 13/547; C08F 4/00; C08F 8/48
See application file for complete search history.

(56) References Cited

U.S. PATENT DOCUMENTS 4,642,329 A * 2/1987 Kirchhoff ............... C07C 13/44
526/284
4,667,004 A 5/1987 Wong
(Continued)

OTHER PUBLICATIONS

Turgut Nugay, et al.; Low Cost Bifunctional Initiators for Bidirectional Living Cationic Polymerization of Olefins. I. Isobutylene; www.polymerchemistry.org; Journal of Polymer Science Part A: Polymer Chemistry 2017, 55, 3716-3724.
(Continued)

*Primary Examiner* — Robert C Boyle
(74) *Attorney, Agent, or Firm* — Renner Kenner Greive Bobak Taylor & Weber

(57) ABSTRACT

In various embodiments, the present invention is directed to a centrally-functionalizable living cationic polymer or copolymer having a centrally-substituted tetraene group having the formula (Continued)

wherein each R is selected from the group consisting of a polymer or a copolymer, such as a polyisobutylene polymer or a poly(isobutylene-b-styrene) copolymer.

22 Claims, 9 Drawing Sheets

(51) Int. Cl.
C08F 220/18 (2006.01)
C08G 65/08 (2006.01)
C08G 77/442 (2006.01)
C07C 13/547 (2006.01)
C07C 13/45 (2006.01)
C08G 65/14 (2006.01)
C08F 110/10 (2006.01)
C08F 293/00 (2006.01)
C08F 4/16 (2006.01)
C08F 212/08 (2006.01)
C08F 210/10 (2006.01)

(52) U.S. Cl.
CPC ............ C08F 8/08 (2013.01); C08F 110/10 (2013.01); C08F 220/18 (2013.01); C08F 293/00 (2013.01); C08G 65/08 (2013.01); C08G 65/14 (2013.01); C08G 77/442 (2013.01); C08F 210/10 (2013.01); C08F 212/08 (2013.01); C08F 2220/1825 (2013.01); C08F 2438/00 (2013.01)

(56) References Cited

U.S. PATENT DOCUMENTS 4,711,964 A * 12/1987 Tan .................. C08G 73/12
528/170
5,869,693 A * 2/1999 Wang .................. C07C 311/21
548/544
2005/0267253 A1 * 12/2005 Hayashi ................ C08G 77/06
524/588

OTHER PUBLICATIONS

R. A. Kirchhoff, et al.; Benzocyclobutenes in Polymer Synthesis; Prog. Polym. Sci., vol. 18, 85-185, 1993.

Nazario Martin, et al.; Organic Preparations and Procedures Int., 23 (2). 237-272 (1991).

Jose L. Segura, et al; o-Quinodimethanes: Efficient Intermediates in Organic Synthesis; Chem. Rev. 1999, 99, 3199-3246.

Goverdhan Mehta, et al; Recent chemistry of benzocyclobutenes; Department of Organic Chemistry, Indian Institute of Science, Bangalore, 500 012, India; Department of Chemistry, Indian Institute of Technology, Powai, Mumbai, 400 076, India; Sep. 26, 2000.

Patricia Garcia-Garcia, et al; Competitive Pathways in the Reaction of Lithium Oxy-orthoquinodimethanes and Fischer Alkoxy Alkynyl Carbene Complexes: Synthesis of Highly Functionalised Seven-Membered Benzocarbocycles; DOI: 10.1002/chem.201002092; Chem. Eur. J. 2011, 17, 564-571.

Yuji Matsuya, et al; Accelerated Electrocyclic Ring-Opening of Benzocyclobutenes under the Influence of a B-Silicon Atom; Faculty of Pharmaceutical Sciences, UniVersity of Toyama, 2630 Sugitani, Toyama 930-0194, Japan, published 2006.

W.R. Roth, et al.; Das Energieprofil des o-Chinodimethan-Benzocyclobuten-Gleichgewichtes; 12 pages, published 1978.

Pierre-Yves Michellys, et al.; Cycloadditions of ortho-Quinodimethanes Derived From Benzocyclobutenes in Organic Synthesis. A Review; http://dx.doi.org/10.1080/00304949609458572, published 1996.

Dale L. Boger, et al.; Diels-Alder Reactions of a-Oxy-o-xylylenes; J. Org. Chem. 1988,53, 5796-5798.

Jana Herzberger, et al.; Polymerization of Ethylene Oxide, Propylene Oxide, and Other Alkylene Oxides: Synthesis, Novel Polymer Architectures, and Bioconjugation; 2015 American Chemical Society; Chem. Rev. 2016, 116, 2170-2243.

* cited by examiner $^1$H NMR spectrum of A-PIB-tetraene-PIB-A (A-PIB-bBCB-PIB-A heated in bulk for 3 hours at 160°C): [$^1$H NMR (CDCl$_3$: δ= 4.62 ppm (s, 1H,a), 4.86 ppm (s, 1H, a'), 4.96-5.1 ppm (br, 2H, c), 5.8-6.0 ppm (br, 1H, b)].

$^1$H-NMR spectrum of epoxidized A-PIB-tetraene-PIB-A [$^1$H NMR (CDCl$_3$): δ= 4.96-5.1 ppm (br, 2H, b), 5.8-6.0 ppm (br, 1H, c), 3 ppm (br, 2H, a)].

$^1$H-NMR spectrum of A-PIB-A(*b*-PEtO) [$^1$H NMR (CDCl$_3$): δ= 4.96-5.1 ppm (br, 2H, b), 5.8-6.0 ppm (br, 1H, c), 3.65 ppm (t, 4H, a)].

$^1$H NMR spectrum of A-PIB-tetraene-PIB-A after Hydrosulfuration with $HSCH_2CH_2OH$: [$^1$H NMR ($CDCl_3$: 3.65 ppm (t, 6H,a,b), 2.65 ppm (t, 6H, c,d ), 2.35-2.45 ppm (d,t, 6H, e,f )].

$^1$H NMR spectrum of A-PIB-tetraene-PIB-A after Hydrosilation with HSi(Me$_2$)-O-Si(Me$_2$)H : [$^1$H NMR (CDCl$_3$: 0.0 ppm (t, 36H,a), 0.4-0.5 ppm (d,t, 6H, b )]

CENTRALLY FUNCTIONALIZABLE LIVING CATIONIC POLYMER OR COPOLYMER AND METHODS OF SYNTHESIZING THE SAME

CROSS-REFERENCE TO RELATED APPLICATIONS

This application claims the benefit of U.S. Provisional Patent Application Ser. No. 62/621,848 entitled "Centrally Functionalized Polyisobutylene" filed Jan. 25, 2018, which is incorporated herein by reference in its entirety.

FIELD OF THE INVENTION

The present invention relates to a living cationic polymer or copolymer. More particularly, the present invention relates to a centrally-functionalizable living cationic polymer or copolymer. Specifically, the present invention relates to a centrally-functionalizable living cationic polymer or copolymer having a centrally-substituted tetraene group.

BACKGROUND OF THE INVENTION

Carbocationic polymerizations in general and living carbocationic polymerizations in particular are of great scientific and practical importance for the creation of useful materials. Living carbocationic polymerizations (LC$^+$Ps) proceed in the absence of chain transfer and termination (collectively termed chain breaking) and lead to well-defined designed useful polymers. LC$^+$Ps lead to predetermined degrees of polymerization (molecular weights), narrow molecular weight distributions, desirable end-groups, and sequential (block, graft, etc.) polymers. The mechanism of LC$^+$Ps is well known in the art. (See, *Designed Polymers by Carbocationic Macromolecular Engineering*, by J. P. Kennedy and B. Ivan, Hanser pub, 1992, the disclosure of which is incorporated herein by reference in its entirety). The chemistry of initiation of cationic polymerizations is discussed in detail in *Carbocationic Polymerization*, by J. P. Kennedy and E Marechal, Wiley, 1982, pp. 81-116, and specifically that of LC$^+$P, pp 9-31, the disclosure of which is incorporated herein by reference in its entirety.

The initiator that is used world-wide for the production of well-defined telechelic PISS (by LC$^+$P of isobutylene) by academic and industrial investigators, is 5-tert-butyl-1,3-bis(1-chloro-1-methylethyl)benzene (abbreviated herein as HDCCl, for hindered dicumyl chloride):

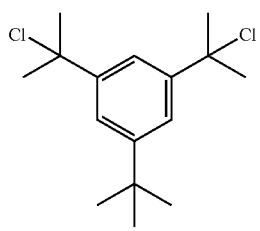

(I)

5-tert-butyl-1,3-bis(1-chloro-1-methylethyl)benzene (HDCCl)

Other initiators commonly used for the synthesis of well-defined telechelic PISS (by LC$^+$P of isobutylene) include those described in U.S. Pat. No. 5,733,998 to Kennedy et al. and U.S. Pat. No. 8,889,926 to Kennedy et al., the disclosure of which are incorporated herein by reference in their entirety.

However, as recently described in PCT Application No. WO2017127642A1, instead of using high cost HDCCl as the initiator, it has been discovered that a bi-directional initiator defined by the formula:

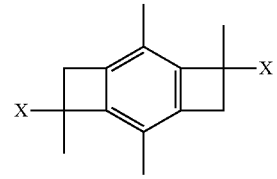

wherein x is Cl, OH, or OCH$_3$ can be used as a low cost initiator.

Traditionally, polyisobutylene (PIB) prepared utilizing a bi-directional initiator, such as bis-benzocyclobutane dichloride (bBCB-diCL) difunctional initiator contains the bis-benzocyclobutane (bBCB) fragment at the center of the macromolecule. If the polymerization is terminated by, for example, allytrimethylsilane (ATMS), the product is ally telechelic PIB having a central bBCB fragment, also known as A-PIB-bBCB-PIB-A, produced according to the synthetic path shown in FIG. 1A.

If the polymerization of the isobutylene is not terminated after complete isobutylene conversion, and styrene is added to the living PIB$^+$, then a triblock polymer having the bBCB fragment in the center of the macromolecule is obtained. The product formed is poly(styrene-b-isobutylene-bCBC-isobutylene-b-styrene), abbreviated PSt-b-PIB-bBCB-PIB-b-PSt, according to the synthetic path shown in FIG. 1B.

Regardless of whether or not HDCCL or the low cost di-functional initiator described above was used for the synthesis of well-defined telechelic PIBs (by LC$^+$P of isobutylene), a centrally-functionalizable polymer or copolymer has not been developed or synthesized that could then be utilized so as to further produce raw materials useful for the synthesis of PIB-based materials exhibiting combinations of useful properties.

SUMMARY OF THE INVENTION

It is one aspect of the present invention to provide a centrally-functionalizable living cationic polymer or copolymer having a centrally-substituted tetraene group having the formula

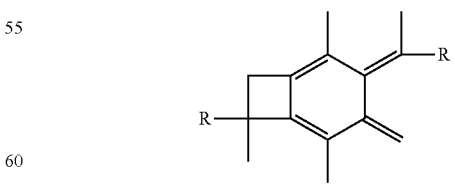

wherein each R is the same and selected from the group consisting of a polymer or a copolymer. In one or more embodiments, each R group is a polyisobutylene polymer. In one or more other embodiments, each R group is a poly(isobutylene-b-styrene) copolymer.

It is another aspect of the present invention to provide a method of synthesizing a centrally-functionalizable living cationic polymer or copolymer having a centrally-substituted tetraene group that includes initiating living cationic polymerization so as to form a non-centrally functionalizable living cationic polymer or copolymer having the formula:

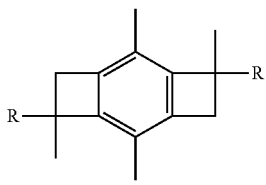

wherein each R group is the same and selected from the group consisting of a polymer or a copolymer, and then thermolyzing the formed non-centrally functionalizable living cationic polymer or copolymer such that a centrally-functionalizable living cationic polymer or copolymer having a centrally-substituted tetraene group is formed having the formula:

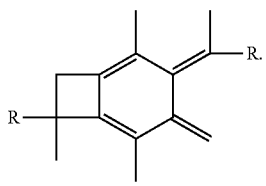

In one or more embodiments, each R group is a polyisobutylene polymer. In one or more other embodiments, each R group is a poly(isobutylene-b-styrene) copolymer. It will be appreciated that, in any formula hereinafter where an R group is provided but not explicitly noted with respect to the formula, each R is a polymer or copolymer, or more particularly, a polyisobutylene polymer or a poly(isobutylene-b-styrene) copolymer.

In one or more other embodiments, the step of initiating in the method above utilizes a bi-directional initiator defined by the formula:

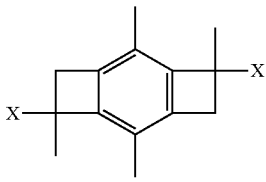

wherein each X is the same and is either Cl, OH, or $OCH_3$.

In one or more other embodiments, the step of thermolyzing in the method above takes place in the presence of a solvent, wherein the solvent is selected from the group consisting of mesitylene, durene, liquid paraffin, paraffin wax, and mineral oil. In other embodiments, the step of thermolyzing may take place in the absence of a solvent.

In further embodiments of the present invention, the methods of the present invention may further include the step of epoxodizing the centrally-functionalizable living cationic polymer or copolymer having a centrally-substituted tetraene group. When this added step is provided, the step of epoxodizing may form a polymer or copolymer having the formula:

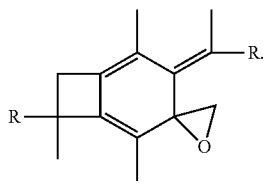

In other further embodiments, the methods of the present invention may include the step of taking the polymer or copolymer formed by the step of epoxodizing and polymerizing said polymer or copolymer with ethylene oxide. Where this is done, the step of polymerizing with ethylene oxide may form a polymer or copolymer having the formula:

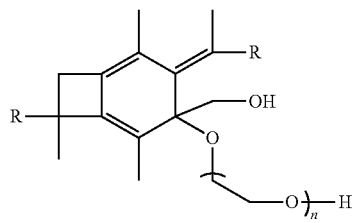

wherein n is a number from 10 to 1000.

In still other embodiments, the methods of the present invention may further include the step of taking the polymer or copolymer formed by the step of epoxodizing and reacting the polymer or copolymer with 2-bromo-2-methyl propionic acid to form an atom transfer radical polymerization macroinitiator having the formula:

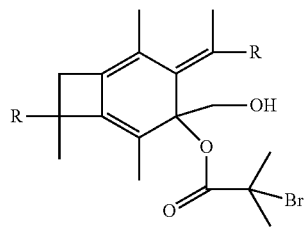

followed by atom transfer radical polymerization with t-butyl acrylate to form a polymer or copolymer having the formula:

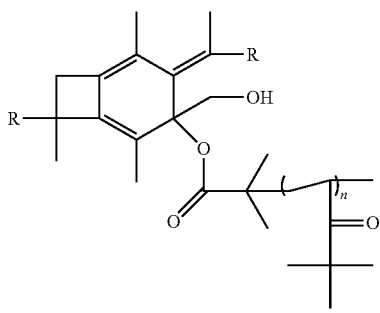

wherein n is a number from 10 to 10,000.

In yet other embodiments, the methods of the present invention may further include reacting with trifluoroacetic acid to form a polymer or copolymer having the formula:

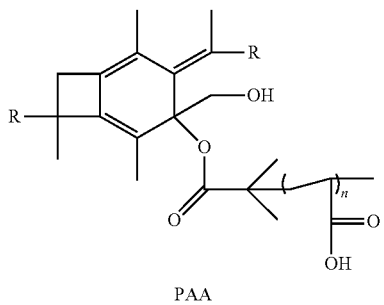

PAA wherein n is a number from 10 to 10,000.

In still other embodiments, the methods of the present invention may further include the step of performing hydrosulfuration on the centrally-functionalizable living cationic polymer or copolymer having a centrally-substituted tetraene group. Where this is done, the step of performing hydrosulfuration may form a polymer or copolymer having the formula:

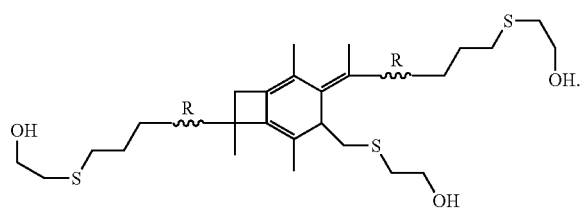

In alternative embodiments, the methods of the present invention may further include the step of performing hydrosilation on the centrally-functionalizable living cationic polymer or copolymer having a centrally-substituted tetraene group. Where this is done, the step of performing hydrosilation may form a polymer or copolymer having the formula:

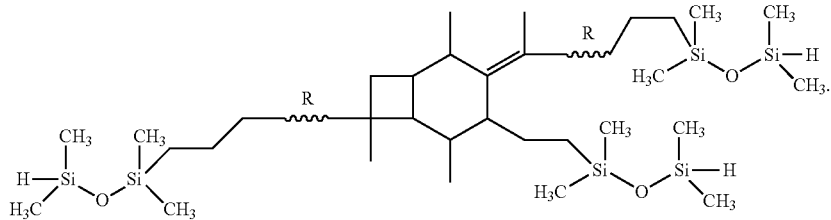

In other alternative embodiments, the method of present invention may further include the step of reacting the centrally-functionalizable living cationic polymer or copolymer having a centrally-substituted tetraene group with a dienophile. When this is done, the step of reacting the centrally-functionalizable living cationic polymer or copolymer having a centrally-substituted tetraene group with a dienophile, such as maleic anhydride, may form a polymer or copolymer having the following formula:

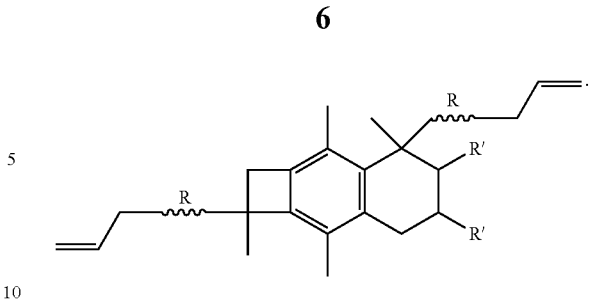

In one or more embodiments, the present invention provides a method of synthesizing a polyurethane utilizing a centrally-functionalizable living cationic polymer or copolymer having a centrally-substituted tetraene group as the starting material, the centrally-functionalizable living cationic polymer or copolymer having a centrally-substituted tetraene group having the formula:

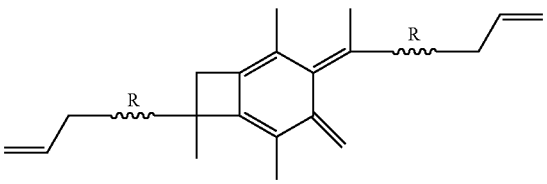

wherein each R is selected from the group consisting of a polymer or a copolymer, and is preferably a polyisobutylene polymer or a poly(isobutylene-b-styrene) copolymer.

BRIEF DESCRIPTION OF THE DRAWINGS

For a more complete understanding of the features and advantages of the present invention, reference is now made to the detailed description of the invention along with the accompanying figures in which.

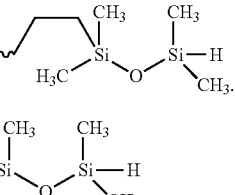

Figure 2:
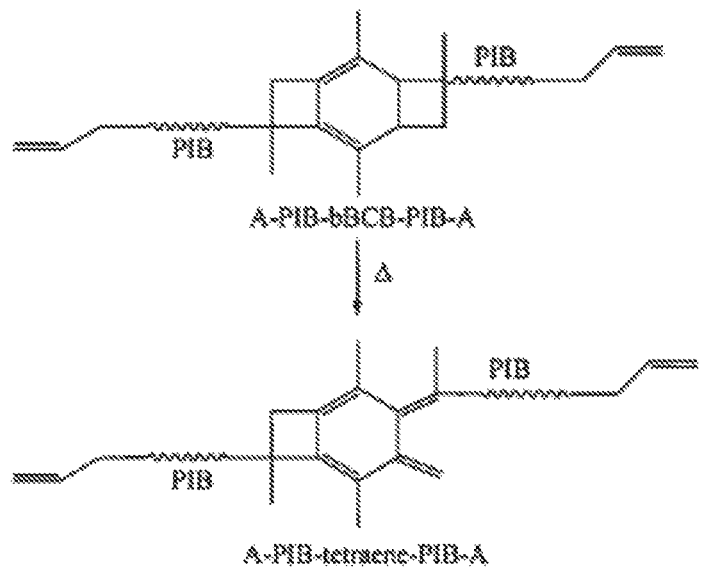
Figure 3:
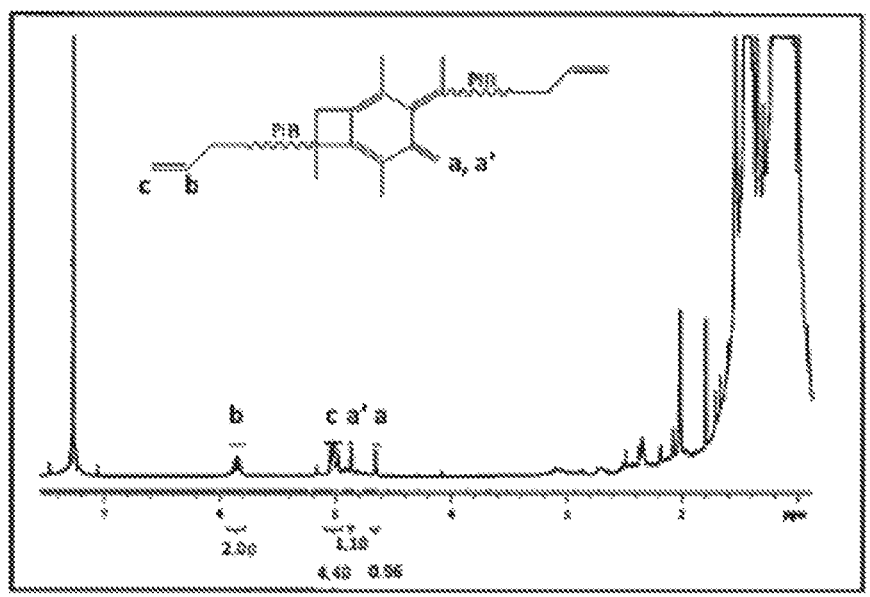
Figure 4:
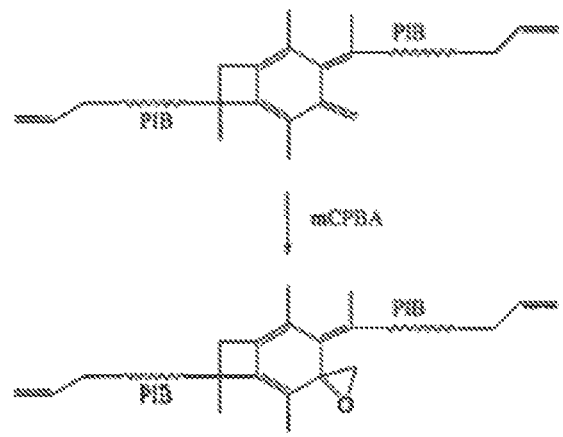
Figure 5:
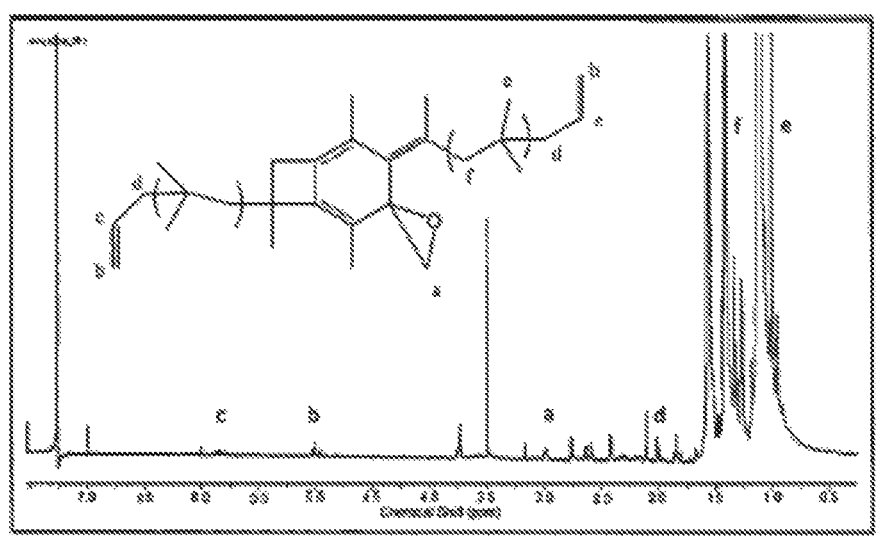
Figure 6:
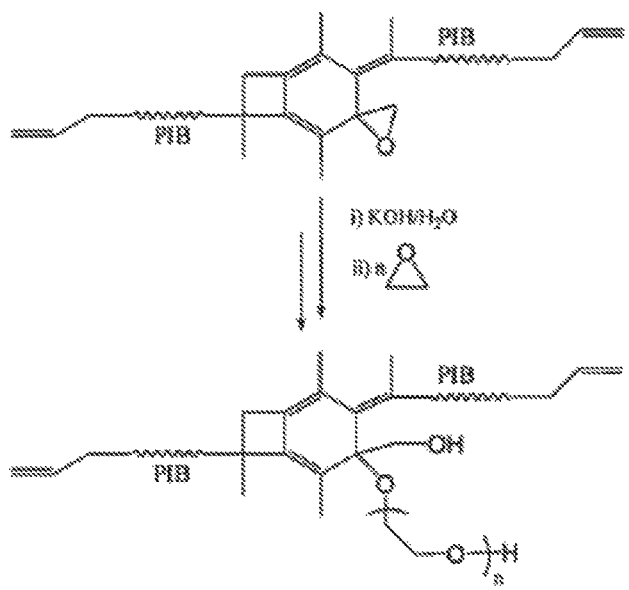
Figure 7:
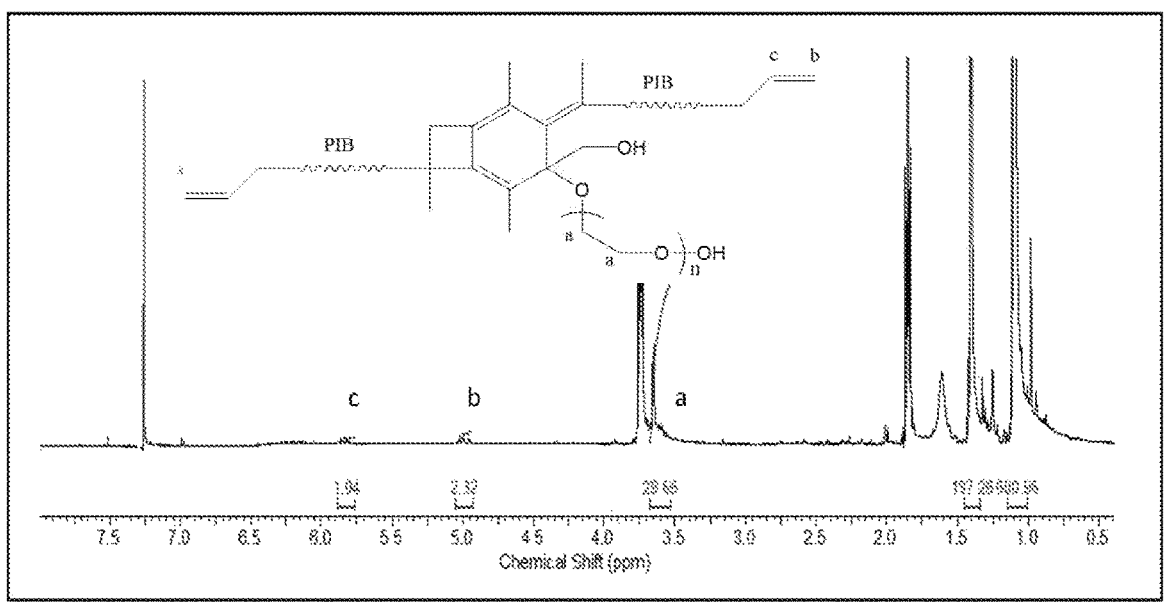
Figure 8:
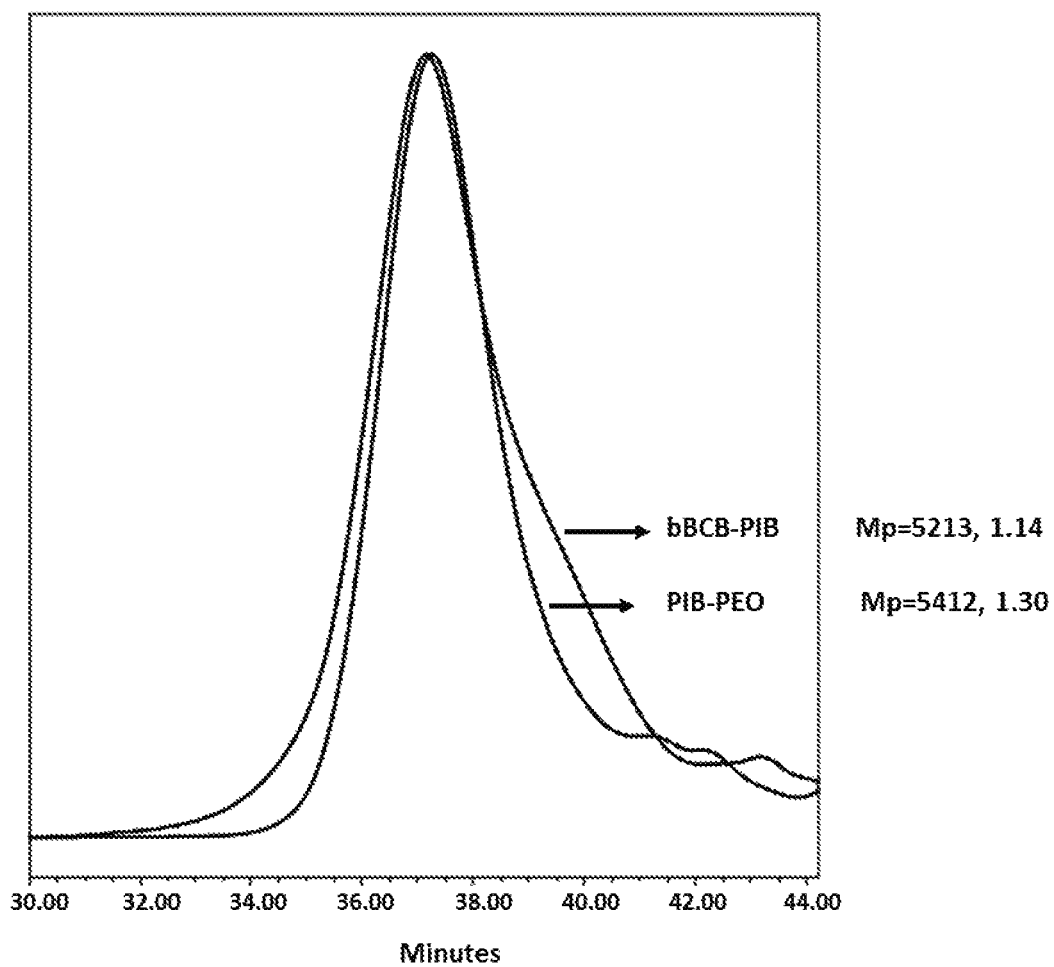
Figure 9:
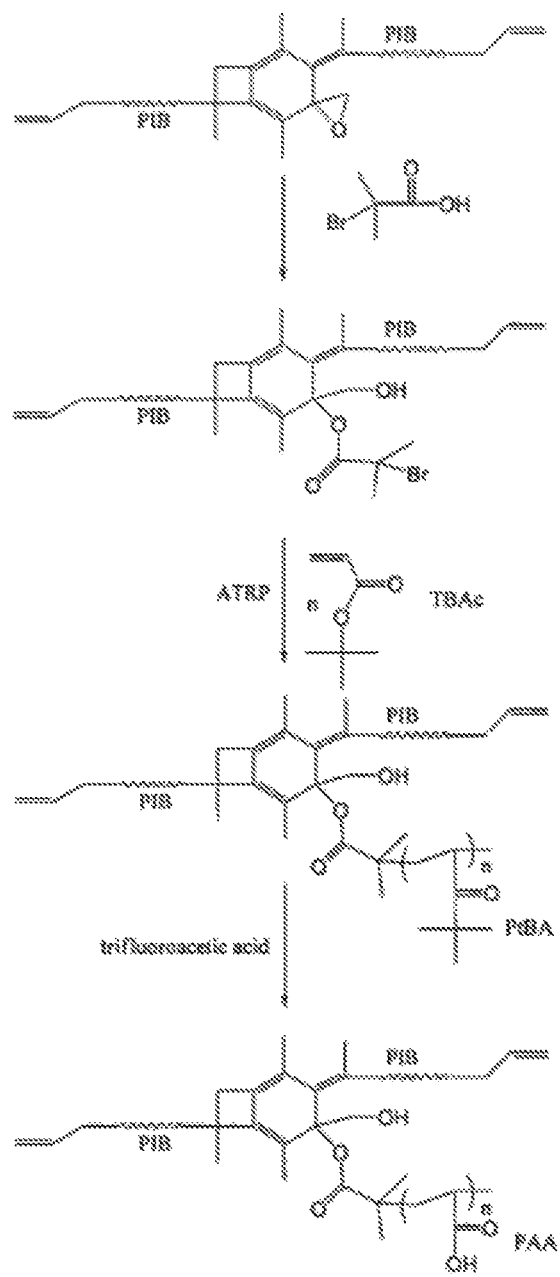
Figure 10:
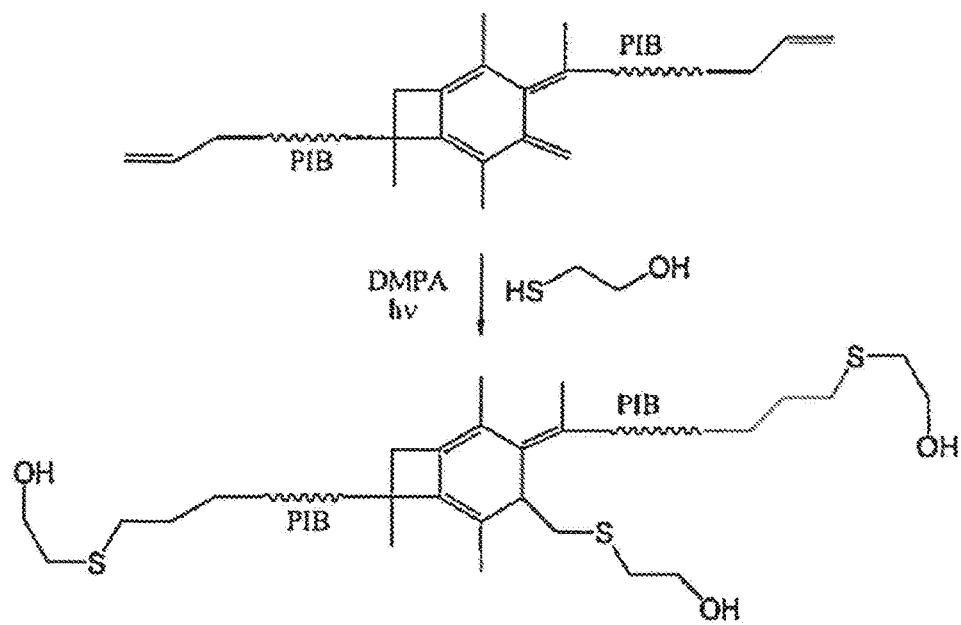
Figure 11:
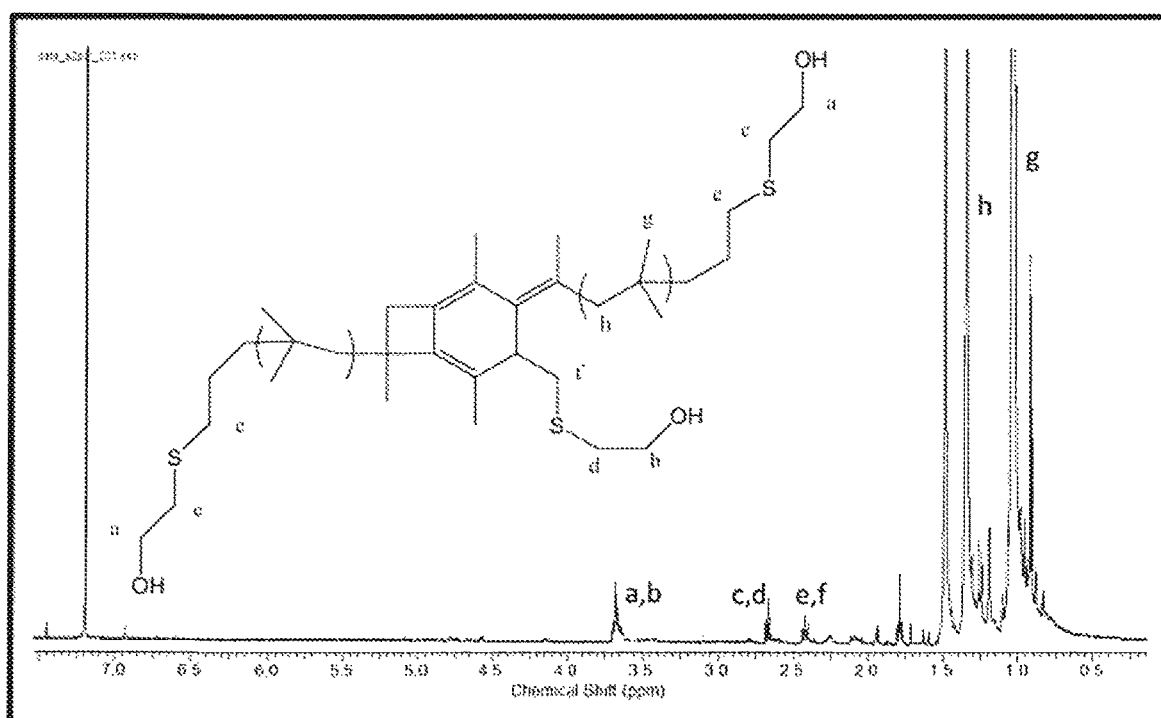
Figure 12:
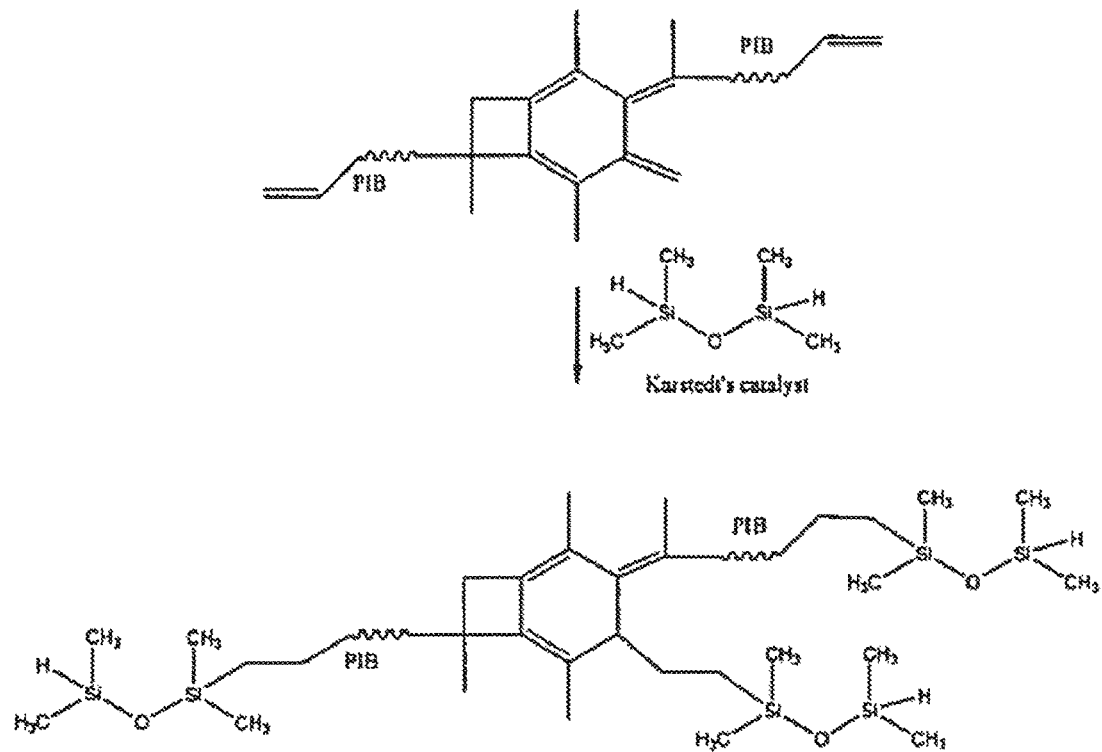
Figure 13:
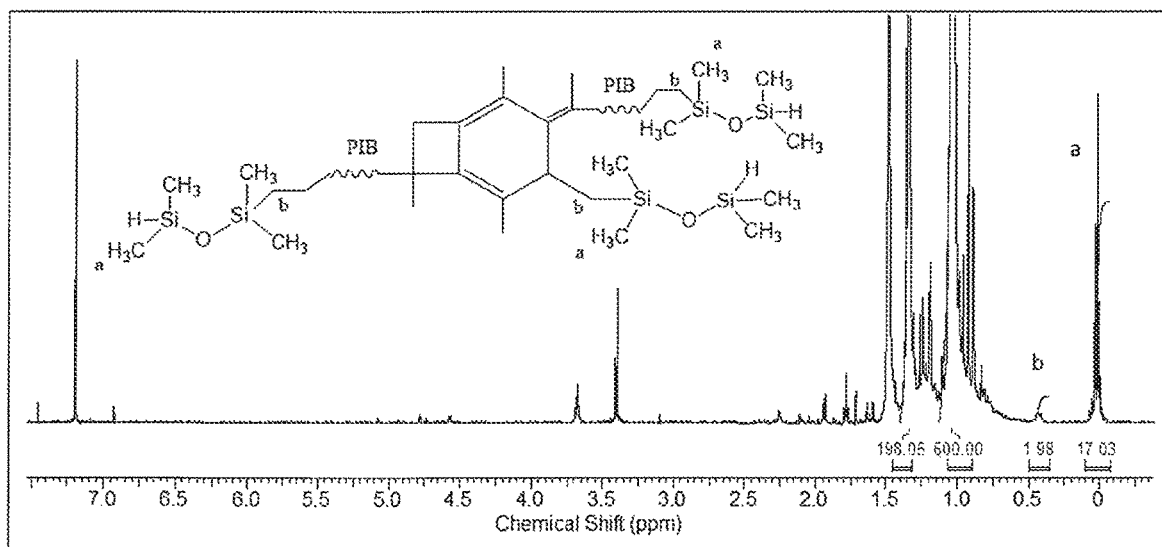
Figure 14:
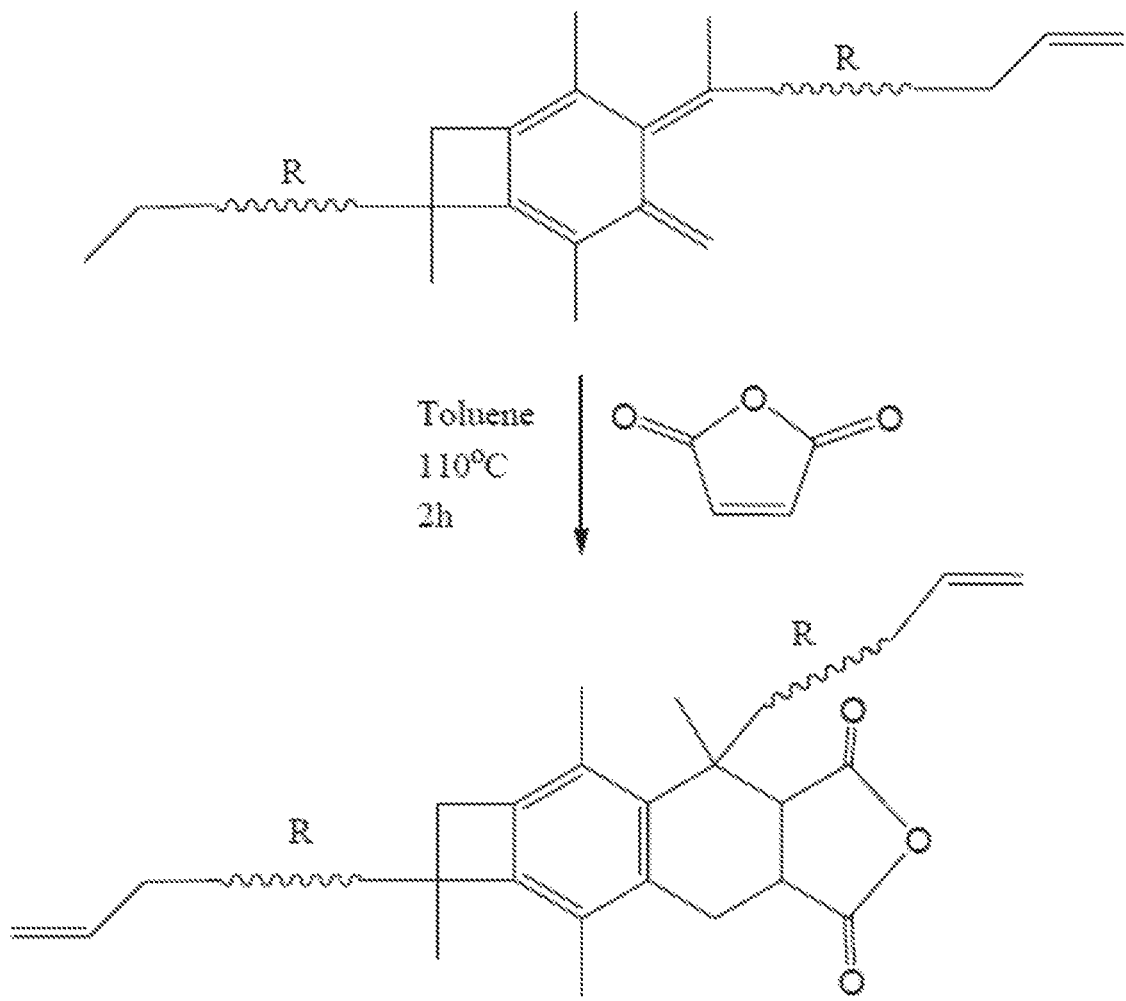

FIG. 2 is a representative synthetic path taken to produce an ally telechelic PIB having a central tetraene fragment, abbreviated as A-PIB-tetraene-PIB-A;

FIG. 3 is an $^1$H NMR spectrum of A-PIB-tetraene-PIB-A made in accordance with the present invention;

FIG. 4 is a representative synthetic path taken to produce epoxidized A-PIB-tetraene-PIB-A made in accordance with the present invention;

FIG. 5 is an $^1$H NMR spectrum of epoxidized A-PIB-tetraene-PIB-A made in accordance with the present invention;

FIG. 6 is a representative synthetic path taken to produce a A-PIB-A(b-PEO) made in accordance with the present invention;

FIG. 7 is an $^1$H NMR spectrum of a A-PIB-A(b-PEO) made in accordance with the present invention;

FIG. 8 is a GPC (RI Detector) trace of a A-PIB-A(b-PEO) made in accordance with the present invention;

FIG. 9 is a representative synthetic path taken to produce A-PIB-A(b-PtBA) and A-PIB-A(b-PAA) made in accordance with the present invention;

FIG. 10 is a representative synthetic path taken to have A-PIB-tetraene-PIB-A undergo hydrosulfuration (Thiol-ene Reaction) with HSC$_2$H$_2$CH$_2$OH made in accordance with the present invention;

FIG. 11 is an $^1$H NMR spectrum of the product obtained when A-PIB-tetraene-PIB-A undergoes hydrosulfuration with HSC$_2$H$_2$CH$_2$OH made in accordance with the present invention;

FIG. 12 is a representative synthetic path taken to have A-PIB-tetraene-PIB-A undergo hydrosilation with 1,1,3,3-tetramethyldisiloxane made in accordance with the present invention;

FIG. 13 is an $^1$H NMR spectrum of the product obtained when A-PIB-tetraene-PIB-A undergoes hydrosilation with 1,1,3,3-tetramethyldisiloxane made in accordance with the present invention; and FIG. 14 is a representative synthetic path taken to react A-PIB-tetraene-PIB-A with maleic anhydride in accordance with the present invention.

DETAILED DESCRIPTION OF ILLUSTRATIVE EMBODIMENTS

The present invention generally relates to a centrally-functionalizable living cationic polymer or copolymer having a centrally-substituted tetraene group. It will be appreciated that an important aspect of the present invention is having a reactive functional group at the statistical center of the polymer or copolymer. Such a polymer or copolymer can then be used, for example, as a novel drug delivery agent or a novel starting material for producing amphiphilic polyurethanes.

In one embodiment of the present invention, to first prepare the centrally-functionalizable living cationic polymer or copolymer having a centrally-substituted tetraene group, a difunctional initiator, such as bis-benzocyclobutane dichloride (bBCB-diCL) difunctional initiator containing a bis-benzocyclobutane (bBCB) fragment at the center of the macromolecule must be prepared. In one embodiment, bBCB-diCL can be prepared according to Scheme 1 below:

Scheme 1

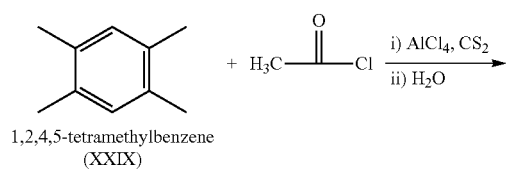

1,2,4,5-tetramethylbenzene
(XXIX)

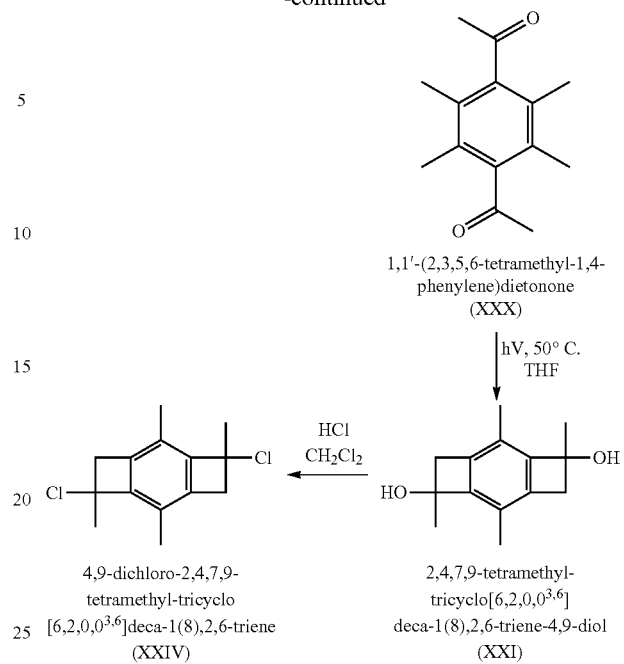

In Scheme 1, above, the starting material is durene (XXIX), but creation of the di-functional initiator is not so limited and suitable starting materials may also include, without limitation, 1,2,4,5-tetramethyl benzene and 1,2,3,5-tetramethyl benzene. The first step involves the Friedel-Crafts diacylation of the starting material with an acetyl halide, such as acetyl chloride (AcCl), acetyl bromide, or acetic anhydride in the presence of aluminum chloride (AlCl$_3$) or a similar Lewis acid, such as FeCl$_3$ or AlBr$_3$, in a suitable solvent such as CS$_2$, dichloromethane, chloroform, chlorobenzene, or nitromathane. (See, e.g., Pinkus A. G., Kalyanam N., Organic Preparations and Procedures Int., 10 (6), 255, 1978 and Andreou A. D., Bulbulian R. V., Gore P. H., Tetrahedron, 36, 2101, 1980 the disclosures of which is incorporated herein by reference in its entirety) and (ii) separating the resulting polymer containing solution into organic and aqueous phases, washing the resulting organic phase with aqueous sodium carbonate (see, Scheme 1) and water, removing the solvent and drying the resulting product to produce the corresponding diethanone, 1,1'-(2,3,5,6-tetramethyl-1,4phenylene) diethanone (diacetyl durene, (DAD)) (molecule (XXX) in Scheme 1).

In a second step, the corresponding diethanone molecule (diacetyl durene, (DAD), molecule (XXX) in Scheme 1) is dissolved in a suitable solvent, such as benzene or tetrahydrofuran (THF) and irradiated with ultraviolet light for a period of from about 48 hours to about 96 hours at a temperature of from about 40° C. to about 60° C. to form the corresponding bis-benzocyclobutenol. In the embodiment of Scheme 1, the bis-benzocyclobutenol is 2,4,7,9-tetramethyl-tricyclo[6.2.0.0$^{3,6}$]deca-1(8),2,6-triene-4,9-diol (bBCB-ol) (molecule (XXI) in Scheme 1).

In a third step, the bis-benzocyclobutenol (see, e.g., molecule (XXI) in Scheme 1) may be hydrochlorinated to form the corresponding dichloro compound (see, e.g., molecule (XXIV) in Scheme 1). In the embodiment of Scheme 1, the corresponding bis-benzocyclobutane dichloride is 4,9-dichloro-2,4,7,9-tetramethyl-tricyclo[6.2.0.0$^{3,6}$]deca-1(8),2,6-triene (XXIV) (bBdClCB). However, other suitable methods known in the art for replacing the OH group with a halogen may also be used in some embodiments.

Once the difunctional initiator, such as bis-benzocyclobutane dichloride, has been prepared, the next step will be to combine the initiator with isobutylene so as to form an ally telechelic PIB having a central bBCB fragment, also known as A-PIB-bBCB-PIB-A, as shown below:

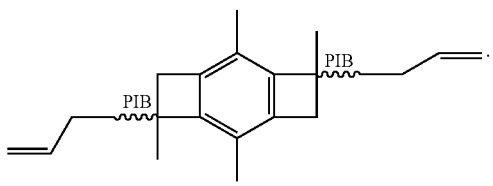

The product shown above is what occurs if the polymerization is terminated by, for example, ATMS. However, in another embodiment of the present invention, if the polymerization of the isobutylene is not terminated, but is allowed to continue until complete IB conversion, and then styrene is added to the living PIB+, then a triblock polymer having the bBCB fragment from the difunctional initiator in the center of the macromolecule is obtained. In this embodiment, the product formed would be poly(styrene-b-isobutylene-bCBC-isobutylene-b-styrene), abbreviated PSt-b-PIB-bBCB-PIB-b-PSt, as shown below:

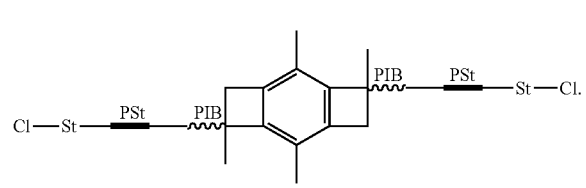

The A-PIB-bBCB-PIB-A product and the PSt-b-PIB-bBCB-PIB-b-PSt product can be abbreviated as R-bBCB-R, where R equals -PIB-A or -PIB-b-PSt.

It has been determined that BCB and BCB-derivatives are readily converted to substituted tetraenes by heating to various temperatures. While BCB and BCB-derivatives are stable at room temperature, the methyl substituted cyclobutane ring is rather unstable above about 160° C. It is theorized that electron-donating groups facilitate the opening of the condensed cyclobutane ring.

With this knowledge, the next step in various embodiments of the present invention is to take either of the R-bBCB-R products and have them undergo thermolysis so that the central bBCB fragment in the R-bBCB-R will be converted into a substituted central tetraene group so as to form a centrally-functionalizable living cationic polymer or copolymer having a centrally-substituted tetraene group identified by the formula:

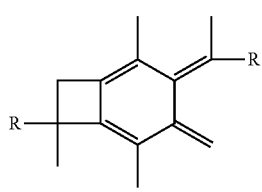

(I)

wherein each R is selected from the group consisting of a polymer or a copolymer, such as for example, a polyisobutylene polymer or a poly(isobutylene-b-styrene) copolymer. For example, FIG. 2 shows the thermolysis of A-PIB-bBCB-PIB-A that produces a A-PIB-tetraene-PIB-A.

In one embodiment of the present invention, the step of thermolysis takes place in the presence of a solvent. The solvent is selected from the group consisting of mesitylene, durene, liquid parrafin, parrafin wax, and mineral oil.

In one embodiment of the present invention, the step of thermolysis takes place in bulk, or in the absence or substantial absence of a solvent.

The tetraene group in the center is highly reactive and can be readily converted to various other functions, such as, but not limited to, epoxy, alcohol, and silane groups, or to various other macroinitiators for the polymerization of various monomers, such as, but not limited to, ethylene oxide, acrylates, styrene, styrene derivatives, and vinyl pyridine. The following discussions will focus on these various other functions and macroinitiators that can be made from the centrally-functionalizable living cationic polymer or copolymer having a centrally-substituted tetraene group discussed above.

In one embodiment of the present invention, molecule (I), having already been formed, will undergo epoxidation in the presence of a peroxycarboxylic acid, such as meta-chloroperoxybenzoic acid (mCPBA) so as to form a polymer or copolymer having the following formula:

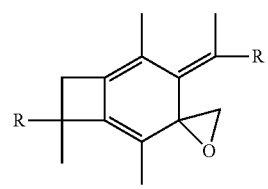

(II)

wherein each R is selected from the group consisting of a polymer or a copolymer, such as for example, a polyisobutylene polymer or a poly(isobutylene-b-styrene) copolymer. The epoxidation of the methylene group versus the non-epoxidation of the terminal allyl groups is due to the much higher reactivity toward epoxidation of the di-substituted exo $CH_2=C$ unsaturation than toward the mono-substituted $CH_2=CH-CH_2-$ group. The second exo $CH_2=C$ unsaturation is tetra-substituted and steric hindrance prevents its peroxidation.

In one embodiment of the present invention, molecule (II), having already been formed, will be polymerized with a material selected from the group consisting of ethylene oxide, propylene oxide, pivalolactone, ε- and δ-lactones so as to form a polymer or copolymer having the following formula:

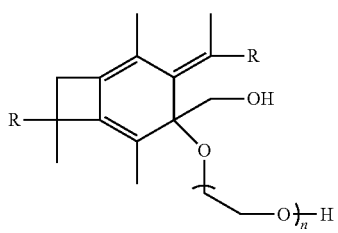

(III)

wherein each R is the same and is selected from the group consisting of a polymer or a copolymer, such as, for example, a polyisobutylene polymer or a poly(isobutylene-b-styrene) copolymer and n is a number from about 10 to about 1,000. For example, if the R group in molecule (III) is a polyisobutylene, then a A-PIB-A(b-PEO) (i.e., allyl-telechelic PIB with a central poly(ethylene oxide) branch) is formed. A-PIB-A(b-PEO) is an amphiphilic A₂B microarm star polymer consisting of a hydrophobic PIB backbone carrying a hydrophilic PEO branch fitted with —CH₂OH end group.

In one embodiment of the present invention, molecule (II) having already been formed will react with 2-bromo-2-methylpropanoic acid or 2-bromopropanoic acid to produce an atom transfer radical polymerization macroinitiator having the following formula:

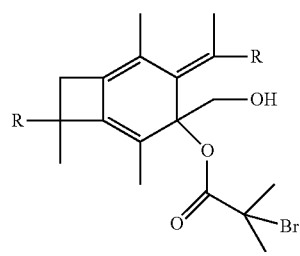

(IV)

wherein R is selected from the group consisting of a polymer or a copolymer, such as, for example, a polyisobutylene polymer or a poly(isobutylene-b-styrene) copolymer. Once molecule (IV) has been formed, it will then be able to undergo atom transfer radical polymerization with t-butyl acrylate, or any vinylic compounds suitable for radical polymerization to form a polymer or copolymer having the formula:

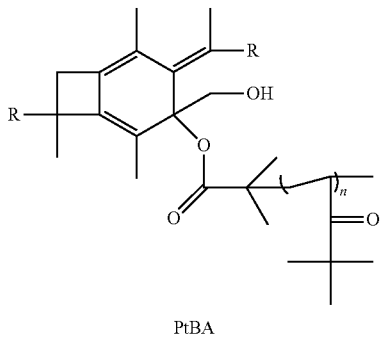

(V)

PtBA wherein R is selected from the group consisting of a polymer or a copolymer, such as, for example, a polyisobutylene polymer or a poly(isobutylene-b-styrene) copolymer and n is a number from about 10 to about 10,000. Although t-butyl acrylate is listed above as being used in the atom transfer radical polymerization, many other monomers can be used for atom transfer radical polymerization such as styrene and its derivatives, methacrylates, N-vinyl pyrrolidone, and vinyl pyridine. Once molecule (V) has been formed, it will then be able to react with trifluoroacetic acid to form a polymer or copolymer having the formula:

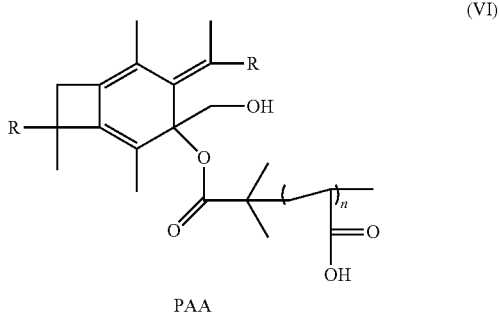

(VI)

PAA wherein R is selected from the group consisting of a polymer or a copolymer, such as, for example, a polyisobutylene polymer or a poly(isobutylene-b-styrene) copolymer and n is a number from about 10 to about 10,000.

In one embodiment of the present invention, molecule (I), having already been formed, will undergo hydrosulfuration to produce a polymer or copolymer having the formula:

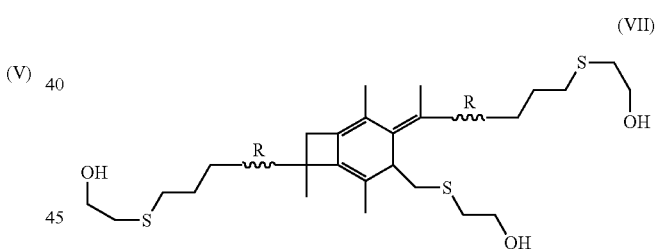

(VII)

wherein R is selected from the group consisting of a polymer or a copolymer, such as, for example, a polyisobutylene polymer or a poly(isobutylene-b-styrene) copolymer.

In one embodiment of the present invention, molecule (I), having already been formed, will undergo hydrosilation to produce a polymer or copolymer having the formula:

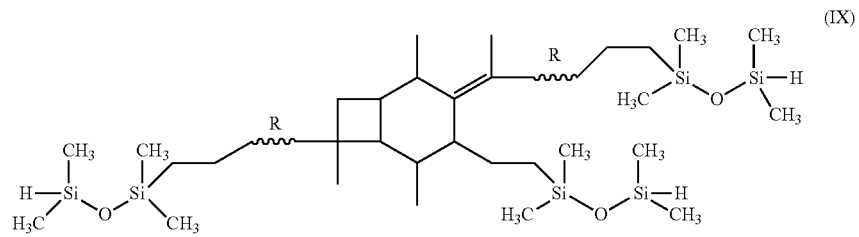

(IX)

wherein R is selected from the group consisting of a polymer or a copolymer, such as, for example, a polyisobutylene polymer or a poly(isobutylene-b-styrene) copolymer.

In one embodiment of the present invention, molecule (I), having already been formed, will react with a dienophile to produce a polymer or copolymer having the formula:

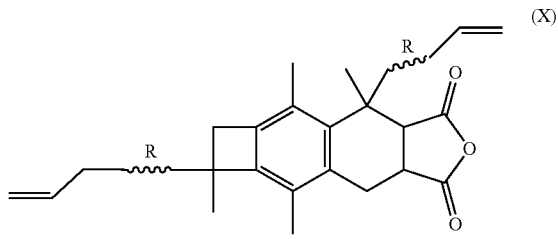

(X)

wherein each R is selected from the group consisting of a polymer or a copolymer, such as, for example, a polyisobutylene polymer or a poly(isobutylene-b-styrene) copolymer. In one or more embodiments, the dienophile is selected from the group consisting of maleic anhydride or maleimide derivatives.

In one embodiment of the present invention, molecule (I), having already been formed, can have the termini in the allyl-telechelic PIBs be readily converted to primary alcohols, by techniques such, as but not limited to, hydroboration with $H_3B$ or anti-Markovnikov hydrobromation. The alcohol-telechelic products formed and their amphiphilic $A_2B$ microarm star derivatives can be used as the starting materials for the synthesis of new polyurethanes. The PIB-based polyurethanes made by the use of alcohol-telechelic $A_2B$ microarm stars having hydrophilic branches display surprising characteristics reflecting both the hydrophobic and hydrophilic constituents, which makes them quite useful as biocompatible biostable delivery depots for amphiphilic drugs.

It has been discovered that the bulk or solution thermolysis of A-PIB-bBCB-PIB-A or PSt-b-PIB-bBCB-PIB-b-PSt rearranges the bBCB initiator fragment and quantitatively produces a substituted tetraene at the statistical center of these macromolecules. This is the first telechelic polymer or copolymer with a central reactive group. The central tetraene group can then be used to convert the polymer or copolymer to various useful functions, such as, but not limited to, epoxy, hydroxyl, and silane, as well as being able to be used to create macroinitiators for the polymerizations of various monomers, such as, but not limited to, ethylene oxide, acrylates, and N-vinyl pyrrolidones.

EXAMPLES

The following experiments are offered to more fully illustrate the invention, but are not to be construed as limiting the scope thereof. Further, while some of experiments may include conclusions about the way the invention may function, the inventors do not intend to be bound by those conclusions, but put them forth only as possible explanations. Moreover, unless noted by use of past tense, presentation of an experiment does not imply that an experiment or procedure was, or was not, conducted, or that results were, or were not actually obtained. Efforts have been made to ensure accuracy with respect to numbers used (e.g., amounts, temperature), but some experimental errors and deviations may be present. Furthermore, although the following experiments may focus on the use of A-PIB-tetraene-PIB-A as the starting material, it should be understood that PSt-b-PIB-tetraene-PIB-b-PSt can just as easily be used as the starting material.

Experiment 1

Thermolysis

Figure 1A:
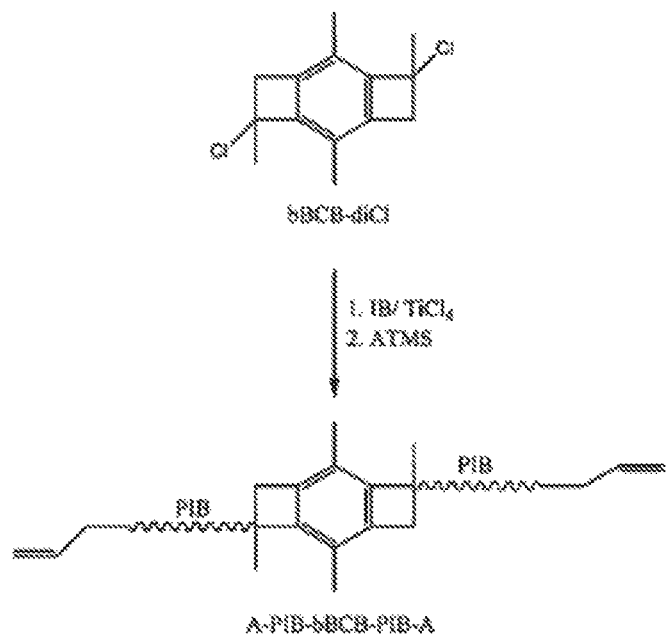
FIG. 1A is a representative synthetic path taken to produce an ally telechelic PIB having a central bBCB fragment, abbreviated as A-PIB-bBCB-PIB-A.
Figure 1B:
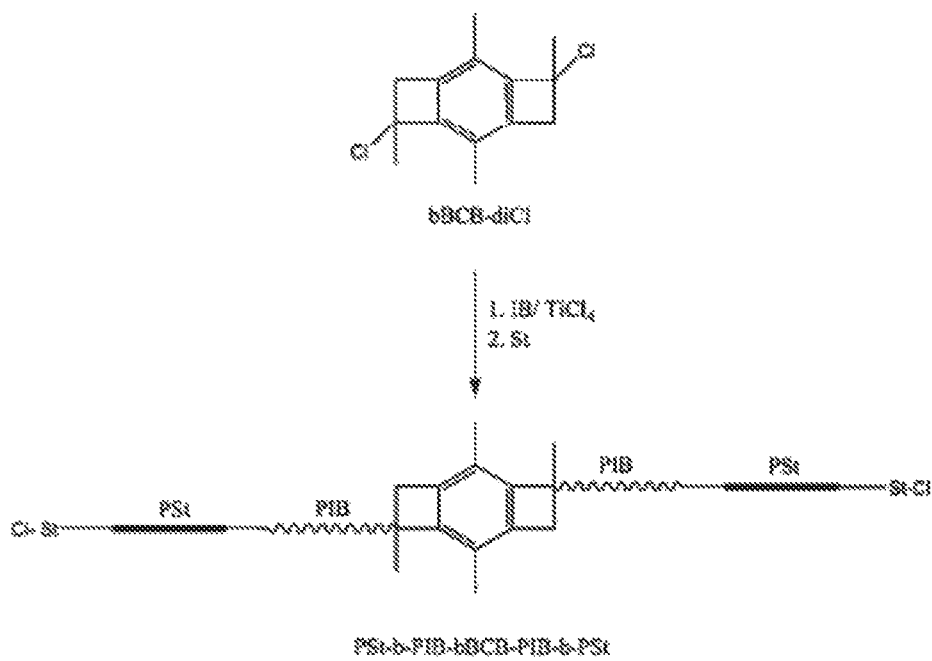
FIG. 1B is a representative synthetic path taken to produce a poly(styrene-b-isobutylene-bCBC-isobutylene-b-styrene), abbreviated PSt-b-PIB-bBCB-PIB-b-PSt.

Preparation of the A-PIB-bBCB-PIB-A occurs according to the synthetic path as shown in FIG. 1A. Specifically, a difunctional initiator, such as bis-benzocyclobutane dichloride (0.10 g, $3.92 \times 10^{-4}$ mol) is combined with isobutylene (1.5 mL, $2.03 \times 10^{-2}$ mol), N,N-dimethyl acetamide (0.68 ml, $7.84 \times 10^{-4}$ mol) and a co-initiator, such as $TiCl_4$ (0.245 mL, $2.25 \times 10^{-3}$ mol) in a hexane/$CH_2Cl_2$ (225/150 mL) mixture at $-80°$ C. The polymerization is then terminated by ATMS (0.93 mL, $5.88 \times 10^{-3}$ mol).

Once prepared, the A-PIB-bBCB-PIB-A will undergo thermolysis according to the synthetic path as shown in FIG. 2A so as to form A-PIB-tetraene-PIB-A as represented by Formula (I) above.

In one example, thermolysis occurs in solution as now described. A 50 ml round bottom flask equipped with a reflux condenser and a magnetic stir bar was charged with a mesitylene solution of A-PIB-bBCB-PIB-A (0.5 g polymer in 10 mL solvent) and the solution was stirred and refluxed ($164°$ C.) for 1 hour, and in a second experiment, for 3 hours, both experiments taking place under a nitrogen atmosphere. Next, the system was cooled to room temperature, the product was precipitated in methanol, re-dissolved in hexane, re-precipitated in methanol, dried, and analyzed by $^1H$ NMR spectroscopy. The results showed that thermolysis of A-PIB-bBCB-PIB-A in refluxing mesitylene for 1 and 3 hours, respectively, gave 0% and 58% cyclobutane ring opening (i.e., A-PIB-tetraene-PIB-A formation).

As thermolysis was found to be incomplete when refluxing in mesitylene even after 3 hours, an additional example was prepared under the same conditions but using durene ($192°$ C.) in the place of the mesitylene solvent. Thus, a blend of 0.5 g of A-PIB-bBCB-PIB-A and 8.7 g of durene (mp: $79.2°$ C.) was heated under a nitrogen atmosphere. The A-PIB-bBCB-PIB-A dissolved completely in the molten durene, and the solution was stirred and refluxed for 1 hour. The solution was cooled to room temperature, the product was precipitated in methanol, re-dissolved in hexane, re-precipitated in methanol, dried, and analyzed by $^1H$ NMR spectroscopy. The results showed that thermolysis of A-PIB-bBCB-PIB-A in refluxing durene for 1 hour produced essentially quantitative ring opening to A-PIB-tetraene-PIB-A. (Quantitative in this context meaning that analysis by 500 MHz $^1H$ NMR spectroscopy shows the expected resonances.) However, as durene is a crystalline solid at room temperature, experimentation with it as a solvent is cumbersome.

In one example, thermolysis occurs in bulk as now described. A thin rubbery sheet of A-PIB-bBCB-PIB-A (~0.5 g) was placed onto a flat steel support and heated at $160°$ C. for 3 hours, and in a second experiment, at $200°$ C. for 2 hours, in an evacuated vacuum oven. Samples were analyzed by $^1H$ NMR spectroscopy. The results showed that thermolysis of A-PIB-bBCB-PIB-A in bulk for 3 hours at $160°$ C. or for 2 hours at $200°$ C., respectively, each produced essentially quantitative ring opening to A-PIB-tetraene-PIB-A. FIG. 3 shows the $^1H$ NMR spectrum of A-PIB-tetraene-PIB-A (A-PIB-bBCB-PIB-A heated in bulk for 3 hours at $160°$ C.) together with assignments. The appearance of resonances at 4.62 ppm and 4.83 ppm indicates the formation of the expected tetraene. Integration of the proton resonances obtained from the newly formed double bond (a, a'=1.1, 0.96 ppm), indicates essentially quantitative (~100%) ring opening.

Experiment 2

Epoxidation of A-PIB-Tetraene-PIB-A

A 50 mL round bottom flask equipped with a reflux condenser and magnetic stir bar was charged with A-PIB-tetraene-PIB-A (0.24 g), mClPBA ($1.1 \times 10^{-4}$ mol, 0.019 g) and $CH_2Cl_2$ (10 mL). The solution was heated to reflux and stirred under a nitrogen atmosphere for 24 hours. The product, epoxidized A-PIB-tetraene-PIB-A, was precipitated in methanol, collected, dried and characterized by $^1H$ NMR spectroscopy. FIG. 4 shows the synthetic path taken to produce the epoxidized A-PIB-tetraene-PIB-A as represented by Formula (II). FIG. 5 shows the $^1H$ NMR spectrum of the epoxidized product.

The absence of resonances in the 4.6-4.9 ppm range indicates the disappearance of the $CH_2=C$ proton and the resonances in the 4.96-6.00 ppm range indicates the presence of terminal allyl groups. These results (i.e., the epoxidation of the methylene group vs. non-epoxidation of the terminal allyl groups) are due to the much higher reactivity toward epoxidation of the di-substituted exo $CH_2=C$ unsaturation than to the mono-substituted $CH_2=CH-CH_2-$ group. The second exo $CH_2=C$ unsaturation is tetra substituted and steric hindrance prevents its peroxidation.

Experiment 3

Polymerization of Epoxidized A-PIB-Tetraene-PIB-A with Ethylene Oxide

Epoxidized A-PIB-tetraene-PIB-A (0.1744 g, 0.0471 mmol) and KOH (3.0 mg, 0.052 mmol) dried at 60° C. at $10^{-2}$ mm Hg were placed in a 100 mL round bottom flask under a nitrogen atmosphere. In a separate flask, 0.56 M $H_2O$ in dry THF was prepared and 0.1 mL of this solution was added to the reaction flask to activate the KOH. Then, THF (10 mL) dried over sodium benzophenone was cryo-distilled into the reaction flask at −78° C. and stirred for 12 hours at 25° C. Ethylene oxide (0.5 mL, 10 mmol) dried over $CaH_2$ was cryodistilled into the reactor. The solution was allowed to come to room temperature and stirred for 3 days. Polymerization was terminated by the addition of acidified methanol. The solvent was evaporated and the product was characterized by $^1H$ NMR spectroscopy and GPC. FIG. 6 shows the synthetic path taken to produce a A-PIB-A(b-PEO) polymer as represented by Formula (III), FIG. 7 shows the $^1H$ NMR spectrum, and FIG. 8 shows the GPC chromatogram.

The $^1H$ NMR spectrum of FIG. 7 shows that the methylene protons of the ethylene oxide appear around 3.50 ppm. The resonances for chain end allylic protons of PIB appear at 4.96-6.00 ppm. The resonances between 1.0 and 1.6 ppm are due to the methylene and methyl protons of the PIB. The GPC of FIG. 8 shows a slight shift of the GPC trace of bBCB-PIB to lower elution times together with the broadening of the PEO-PIB trace which indicates the addition of the PEO chain. The shoulder at the low MW side may be due to some unreacted PIB in the system.

Experiment 4

Reaction of Epoxidized A-PIB-Tetraene-PIB-A with 2-Bromo-2-Methyl Propionic Acid to Produce an ATRP Macroinitiator, Followed by ATRP of t-Butyl Acrylate In the first step of this synthesis, epoxidized A-PIB-tetraene-PIB-A (1.0 g, 0.27 mmol) and anhydrous toluene (20 mL) are placed in a 100 ml round bottom flask under nitrogen atmosphere. Then, 2-bromo-2-methyl propionic acid (0.27 g, 1.62 mmol) is added to the solution and the reaction mixture is stirred for 12 hours at 100° C. The solution is cooled to room temperature and the product is precipitated in methanol. This purification is repeated several times. The product, bromoalkyl-functionalized PIB macroinitiator, as represented by Formula (IV), is dried and characterized by $^1H$ NMR spectroscopy and FTIR.

Subsequently, the PIB macroinitiator (1.0 g, 0.27 mmol), Cu(I)Br (0.02 g, 0.14 mmol), N,N,N',N''-pentamethyldiethylenetriamine (PMDETA) (0.06 g, 0.35 mmol) and toluene (50 ml) are placed in a 100 mL Schelenk flask. The reaction mixture is degassed by bubbling nitrogen for 30 minutes. Then, tert-Butyl acrylate (1.35 g, 10.6 mmol) (targeted Mn for a 5,000 g/mol PtBua block) is transferred into the flask via a nitrogen-purged syringe. Polymerization is conducted for ~24 hours at 55° C. under magnetic stirring. After completion of the polymerization, the reaction mixture is diluted with 100 mL THF and stirred for 48 hours over 3.5 g of "DOWEX MSC-H" n ion exchange resin (more than 10 times excess of acid sites of resin against the initial amount of CuBr). The resulting solution is filtered through a column packed with neutral alumina to remove traces of the catalyst. The filtrate is concentrated by rotary evaporation and precipitated into methanol. The product, as represented by Formula (V), is dried and characterized by $^1H$ NMR spectroscopy and FTIR.

Next, in a 100 mL Schelenk flask, trifluoroacetic acid (13.9 mL, 180 mmol) is slowly added to the solution of $A_2B$ microarm star PIB-PTBA polymer (0.27 mmol) in 2.1 mL of anhydrous dichloromethane at 0° C. The reaction mixture is kept under magnetic stirring at this temperature for 1 hour, then 2 days at room temperature. The product, as represented by Formula (VI), is precipitated into diethylether and the copolymer is dried under vacuum. FIG. 9 shows the synthetic path as discussed above for Experiment 4.

Experiment 5

Hydrosulfuration (Thiol-ene Reaction) of A-PIB-tetraene-PIB-A with $HSC_2H_2CH_2OH$ A-PIB-tetraene-PIB-A (0.1 g, 0.027 mmol), DMPA (28.1 mg, 0.11 mmol) and THF (5 mL) were placed in a 50 mL round bottom flask and stirred in the dark for half an hour until a homogeneous solution was obtained. The system was cooled by a water-ice bath, $HSCH_2CH_2OH$ (13.6 mg, 0.17 mmol) was added, the mixture was the stirred for a few minutes, and irradiated for 60 minutes in a UV chamber equipped with 365 nm lamps and an air circulating system. The crude product, as represented by Formula (VII), was precipitated into excess methanol, decanted and dried in a vacuum at 40° C. The product was characterized by $^1H$ NMR spectroscopy. FIG. 10 outlines the synthetic path taken to arrive at the —$CH_2OH$-telechelic PIB having a pendant —CH$_2$OH group at the center of the polymer which forms upon hydrosulfuration of A-PIB-tetraene-PIB-A with HSCH$_2$CH$_2$OH.

The $^1$H NMR spectrum of the product is shown in FIG. 11. The —S—CH$_2$—CH$_2$—OH proton appears at the 2.22 ppm at a triplet. The triplet at 2.57 and 2.82 ppm are associated with methylene protons adjacent to sulfur and the doublet of triplets at 3.80 ppm is due to methylene protons adjacent the hydroxyl group. The resonances between 0 and 1.8 ppm are due to methylene protons of PIB. Disappearance of double bond peaks arising from both allylic chain ends (5.00 ppm and 5.83 ppm) and themolyzed initiator fragments (4.63 ppm and 4.84 ppm) indicates successful functionalization.

Experiment 6

Hydrosilation of A-PIB-Tetraene-PIB-A with 1,1,3,3-Tetramethyldisiloxane

A-PIB-tetraene-PIB-A (0.1 g, 0.027 mmol), 1,1,3,3-tetramethyldisiloxane (27 mg, 0.20 mmol), and Karstedt's catalyst (10 μL) were placed in a 50 mL round bottom flask containing THF (5 mL). The solution was stirred for 4 hours at 25° C., the product was precipitated into excess methanol, decanted and dried in vacuum at 40° C. The product, as represented by Formula (IX), was characterized by $^1$H NMR spectroscopy.

FIG. 12 outlines the synthetic path taken to hydrosilate the A-PIB-tetraene-PIB-A with HSi(Me$_2$)—O—Si(Me$_2$)H. The $^1$H NMR spectrum of the product is shown in FIG. 13. The methyl protons of —Si(Me$_2$)—O—Si(Me$_2$)H appear around 0.00 ppm. The resonance for CH$_2$ that forms upon hydosilation appears at 0.4 ppm. The resonance between 0 and 1.8 ppm are due to the methylene protons of PIB. The disappearance of double bond resonances due to the two allylic chain ends (5.00 ppm and 5.83 ppm) and thermolyzed initiator fragment (4.63 ppm and 4.84 ppm) indicates a successful hydrosilation reaction.

Experiment 7

Reaction of A-PIB-Tetraene-PIB-A with a Dienophile (Maleic Anhydride)

A 50 mL round bottom flask equipped with a reflux condenser and magnetic stir bar was charged with A-PIB-tetraene-PIB-A (0.25 g, 0.068 mmol), maleic anhydride (0.021 g, 2.1×10$^{-4}$ mol), and toluene (10 mL). The solution was heated to reflux and stirred under a nitrogen atmosphere for 2 hours. The product, as represented by Formula (X), was precipitated in methanol, collected, dried, and examined by NMR spectroscopy. FIG. 14 outlines the synthetic path taken to react the A-PIB-tetraene-PIB-A with maleic anhydride.

In light of the foregoing, it should be appreciated that the present invention significantly advances the art by providing a centrally-functionalizable living cationic polymer or copolymer having a centrally-substituted tetraene group and method of making the same that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A centrally-functionalizable living cationic polymer or copolymer having a centrally-substituted tetraene group having the formula

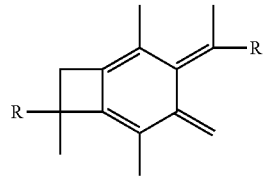

wherein each R is the same and selected from the group consisting of a polymer or a copolymer.

2. The centrally-functionalizable living cationic polymer or copolymer of claim 1, wherein each R is a polyisobutylene polymer.

3. The centrally-functionalizable living cationic polymer or copolymer of claim 1, wherein each R is a poly(isobutylene-b-styrene) copolymer.

4. A method of synthesizing a centrally-functionalizable living cationic polymer or copolymer having a centrally-substituted tetraene group comprising:

a. initiating living cationic polymerization so as to form a non-centrally functionalizable living cationic polymer or copolymer having the formula:

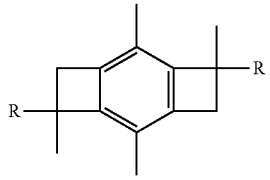

wherein each R is the same and selected from the group consisting of a polymer or a copolymer; and b. thermolyzing the formed non-centrally functionalizable living cationic polymer or copolymer such that a centrally-functionalizable living cationic polymer or copolymer having a centrally-substituted tetraene group is formed having the formula:

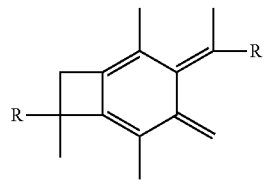

wherein each R is the same and selected from the group consisting of a polymer or a copolymer.

5. The method of claim 4, wherein each R is a polyisobutylene polymer.

6. The method of claim 4, wherein each R is a poly (isobutylene-b-styrene) copolymer.

7. The method of claim 4, wherein the step of initiating utilizes a bi-directional initiator defined by the formula:

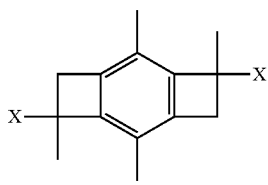

wherein X is the same and selected from the group consisting of Cl, OH, and OCH₃.

8. The method of claim 4, wherein the step of thermolyzing takes place in the presence of a solvent and wherein the solvent is selected from the group consisting of mesitylene, durene, liquid paraffine, paraffine wax, and mineral oil.

9. The method of claim 4, wherein the step of thermolyzing takes place in the absence of a solvent.

10. The method of claim 4, further comprising the step of epoxodizing the centrally-functionalizable living cationic polymer or copolymer having a centrally-substituted tetraene group.

11. The method of claim 10, wherein the step of epoxodizing forms a polymer or copolymer having the formula:

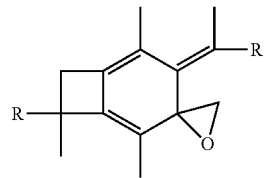

wherein each R is the same and selected from the group consisting of a polymer or a copolymer.

12. The method of claim 11, further comprising the step of taking the polymer or copolymer formed by the step of epoxodizing and polymerizing said polymer or copolymer with ethylene oxide.

13. The method of claim 12, wherein the step of polymerizing with ethylene oxide forms a polymer or copolymer having the formula:

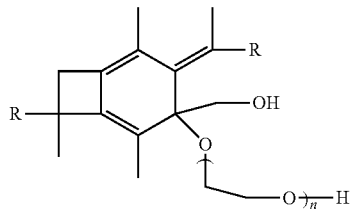

wherein n is a number from 10 to 1,000 and wherein each R is the same and selected from the group consisting of a polymer or a copolymer.

14. The method of claim 11, further comprising the step of taking the polymer or copolymer formed by the step of epoxodizing and reacting the polymer or copolymer with 2-bromo-2-methyl propionic acid to form an atom transfer radical polymerization macroinitiator having the formula:

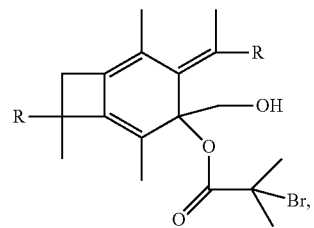

wherein each R is the same and selected from the group consisting of a polymer or a copolymer, followed by atom transfer radical polymerization with t-butyl acrylate to form a polymer or copolymer having the formula:

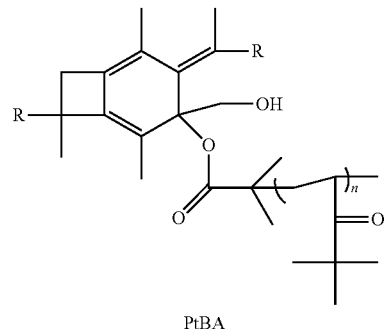

PtBA wherein n is a number from 10 to 10,000 and wherein each R is the same and selected from the group consisting of a polymer or a copolymer.

15. The method of claim 14, further comprising reacting with trifluoroacetic acid to form a polymer or copolymer having the formula:

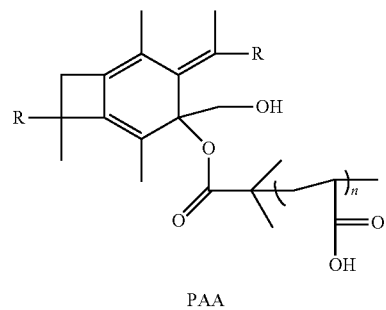

PAA wherein n is a number from 10 to 10,000 and wherein each R is the same and selected from the group consisting of a polymer or a copolymer.

16. The method of claim 5, further comprising the step of performing hydrosulfuration on the centrally-functionalizable living cationic polymer or copolymer having a centrally-substituted tetraene group.

17. The method of claim 16, wherein the step of performing hydrosulfuration forms a polymer or copolymer having the formula:

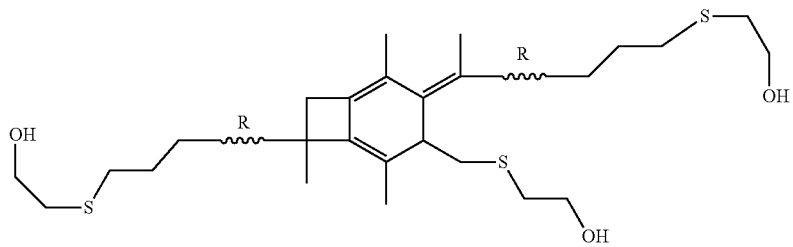

wherein each R is the same and selected from the group consisting of a polymer or a copolymer.

18. The method of claim 5, further comprising the step of performing hydrosilation on the centrally-functionalizable living cationic polymer or copolymer having a centrally-substituted tetraene group.

19. The method of claim 18, wherein the step of performing hydrosilation forms a polymer or copolymer having the formula:

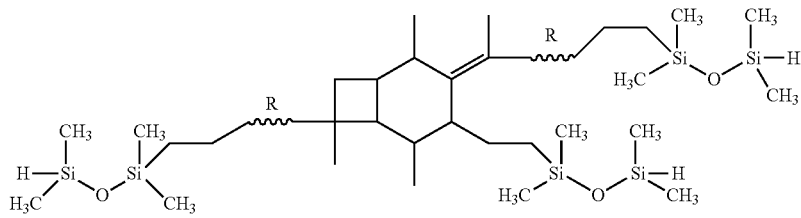

wherein each R is the same and selected from the group consisting of a polymer or a copolymer.

20. The method of claim 4, further comprising the step of reacting the centrally-functionalizable living cationic polymer or copolymer having a centrally-substituted tetraene group with a dienophile.

21. The method of claim 20, wherein the step of reacting the centrally-functionalizable living cationic polymer or copolymer having a centrally-substituted tetraene group with a dienophile forms a polymer or copolymer having the following formula:

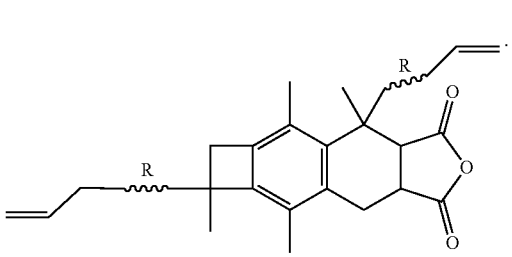

wherein each R is the same and selected from the group consisting of a polymer or a copolymer.

22. A method of synthesizing a polyurethane utilizing a centrally-functionalizable living cationic polymer or copolymer having a centrally-substituted tetraene group as the starting material, the centrally-functionalizable living cationic polymer or copolymer having a centrally-substituted tetraene group having the formula:

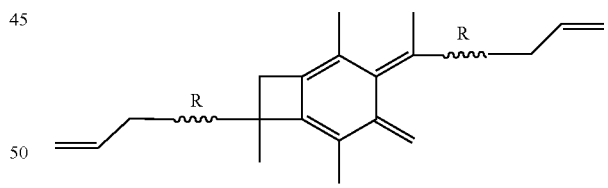

wherein each R is selected from the group consisting of a polymer or a copolymer.

* * * * *